United States Patent [19]

Kaufmann

[11] Patent Number: 4,735,502

[45] Date of Patent: Apr. 5, 1988

[54] REUSABLE PLASTIC CUVETTE ARRAY

[75] Inventor: F. Kim Kaufmann, Sussex, Wis.

[73] Assignee: Medatron, Inc., Sussex, Wis.

[21] Appl. No.: 933,166

[22] Filed: Nov. 21, 1986

[51] Int. Cl.$^4$ .............................................. G01N 21/07
[52] U.S. Cl. .................................... 356/246; 356/427
[58] Field of Search ............... 356/246, 244, 427, 440; 422/64, 72; 436/45

[56] References Cited

U.S. PATENT DOCUMENTS

| | | |
|---|---|---|
| 4,123,173 | 10/1978 | Bullock et al. |
| 4,226,531 | 10/1980 | Tiffany et al. |
| 4,314,970 | 2/1982 | Stein et al. |
| 4,373,812 | 2/1983 | Stein et al. |
| 4,387,992 | 6/1983 | Swartz ............................. 356/246 |
| 4,580,897 | 4/1986 | Nelson et al. ........................ 356/246 |

Primary Examiner—Eugene R. LaRoche
Assistant Examiner—Robert J. Pascal
Attorney, Agent, or Firm—Thomas C. Sylke; John C. Cooper, III; Fred Wiviott

[57] ABSTRACT

A rotatable cuvette array made of PETG plastic for mixing two substances has a circular lower section with a number of circumferentially spaced cuvettes each having inner and outer compartments, both of which have upwardly diverging walls, and a ramp separating the two compartments. The edges and corners of the cuvettes are rounded to provide additional strength through increased thickness at those points. The upper section of the cuvette array is a disc having alternating opaque and transparent portions providing optic pathways through only the outer compartments of each cuvette. The upper section also includes a number of holes which provide access to each inner and outer compartment of each cuvette for filling. The upper and lower sections are separable to permit cleaning and subsequent reattachment so that each cuvette array is reusable.

16 Claims, 2 Drawing Sheets

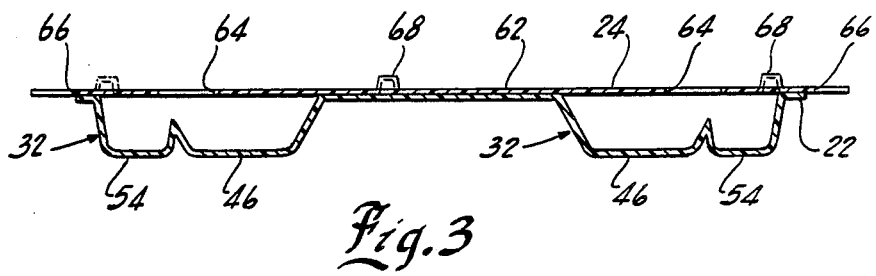
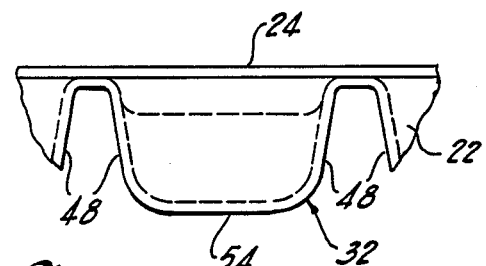
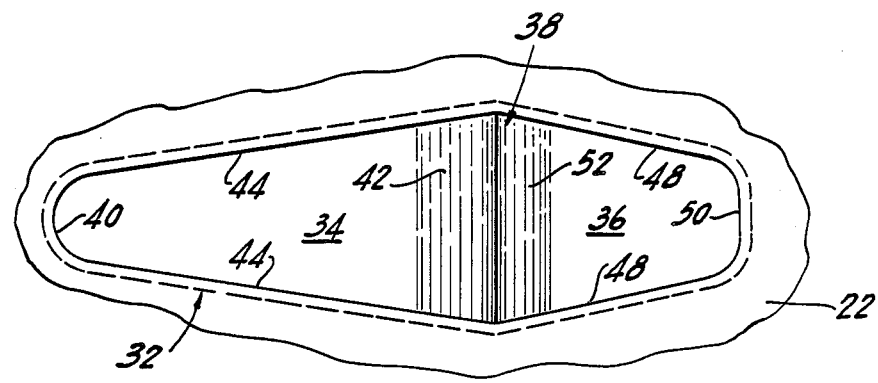
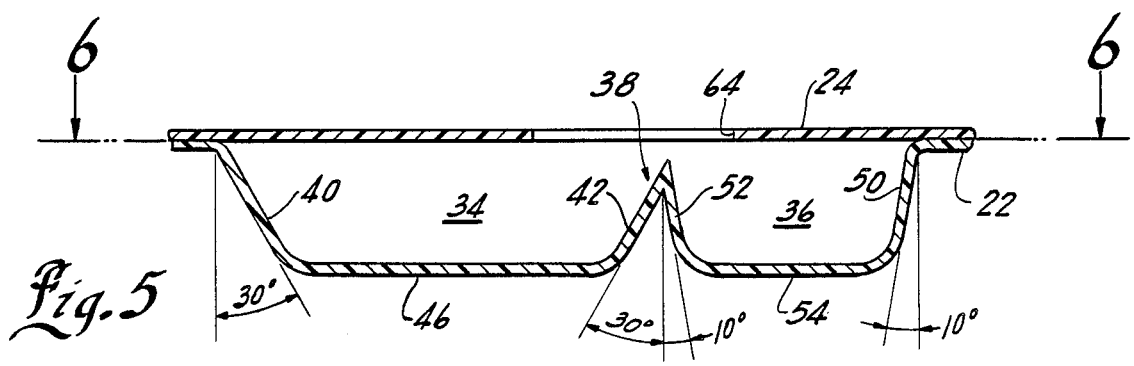

REUSABLE PLASTIC CUVETTE ARRAY

BACKGROUND OF THE INVENTION

1. Field of the Invention

The invention relates generally to rotatable disc cuvette arrays adapted for use in a centrifugal analyzer having means to rotate the array so as to permit measurements of the optical density or absorbence values of light passing successively through each of a series of radially spaced cuvettes during their rotation. In particular, the invention relates to a reusable cuvette array which may be used for chemical analysis, disassembled, easily cleaned and used again.

2. Description of Related Art

Analyzing systems using rotating cuvette arrays are in wide use, particularly for absorbence measurements in connection with analytical apparatus.

Generally, earlier arrays have consisted of an array composed of a number of wedge-shaped, radially disposed cuvettes which extend out from a central hub and which contain, extending radially outwardly from the hub, the following elements: a first annular series of compartments for holding a first substance; an annular series of dividing walls or ramps, one for each cuvette; a second annular series of compartments for holding a second substance which is frequently an unknown sample of blood or other body fluid; and an annular series of vertical end walls. To conduct analysis, the array is rotated at a speed designed to cause the contents of the first chamber of each cuvette to climb over the ramp under centrifugal force and mix and react with the material contained in the second chamber.

A cover is usualy placed over the cuvettes to reduce evaporation and contamination and still provide optical paths so that the contents of the second chamber after reaction may be analyzed through photometric means.

One example of an improvement to this general prior configuration is found in U.S. Pat. No. 4,123,173 issued to Bullock, et al on Oct. 31, 1978. The Bullock array is a less expensive cuvette array compared to those that preceeded it. In selecting materials to help achieve this lower cost, the Bullock device was designed to be disposable, i.e., each cuvette is to be used only once. The Bullock array consists of a number of wedge-shaped cuvettes which are formed by sheet molding. The cuvettes are separate from one another and are divided into an inner and outer pair of compartments. The compartments are divided by a ramp-shaped wall which is inclined on its inner surface while essentially vertical on its outer surface. The outer end of the outer compartment is configured so that fluids flowing outwardly under centrifugal force are forced in toward the radial center by reverse curved side and end walls. This is designed to promote intimate mixing. Further outside the end walls of the cuvettes is a horizontal annular flange.

Circumferentially bonded to this flange is a flexible horizontal annulus formed of thin plastic material having light transmissive properties. The annulus overlies the cuvette end walls and is provided with slots on both its inner edge and outer edge. The slots on the outer edge are provided as an encoding system and are used to provide a zero referencing of the reading of each cuvette during analysis. Bullock, et al provides that the outer portion of the annulus with these encoding slots be made opaque by painting or some other means. The inner edge of the annulus extends to a point just inside the inner ramp wall. The slots provided along this inner edge extend just far enough outward to provide access to the outer compartment.

Both the upper horizontal annulus and the lower cuvette array piece are formed of a thin, flexible thermoplastic material which is generally transparent and which has a high degree of flexibility.

There are several drawbacks however to the configuration used in Bullock, et al. First, the thin plastic material forming the bottom cuvette array portion is so thin that there frequently are breaks and cracks in the outer compartments at the points where severe bending of the plastic occurs during forming. For example, the end walls form a right angle with the lower surface of the outer compartment. At these points the plastic is so thin that cracking and dimpling is a frequent problem. Small leaks in a device which makes measurements based on microliters can create gross inaccuracies in the results. Therefore, improvements with respect to the material and the formation of the cuvettes themselves would be important. Second, the upper horizontal annulus leaves open a considerable amount of the inner compartment of each cuvette. This permits for evaporation and cross-contamination frequently because of splashing. In addition, when either substance is pipetted into one of the compartments, the liquid enters with such force that it frequently splashes; and, unless adequate covering is provided, the splashing will either cause contamination to adjoining cuvettes, or will at least adversely alter the proper proportioning needed for accurate test results. Finally, it would be advantageous to have a disc which is as inexpensive as the Bullock, et al device but would nonetheless be reusable and could be cleaned easily and conveniently after use.

Another multi-cuvette array is shown in U.S. Pat. No. 4,226,531 issued to Tiffany, et al on Oct. 7, 1980. Tiffany, et al shows, like Bullock, et al, a lower cuvette segment and an upper annulus. These two elements are welded together to form a single disposable plastic array. Once again, the array is designed to be thrown away after one use and cannot conveniently be cleaned.

The design in Tiffany is constructed by injection molding and subsequent welding of the lower cuvette array to the upper planar member. Being welded together, the two elements are not readily cleanable. In addition, the square corners and right angle edges shown in Tiffany do not aid mixing as effectively as would rounded edges and corners.

Two patents which incorporate the general structure of Tiffany are U.S. Pat. Nos. 4,314,970 issued Feb. 9, 1982 to Stein, et al and 4,373,812 issued Feb. 15, 1983 to Stein, et al. The Stein '812 patent incorporates Tiffany almost exactly except that capillary flow inhibiting structure has been added t the inner lower edges of each cuvette to help prevent capillary flow during rotation and analysis. The Stein, et al '970 patent, while using the basic Tiffany structure, is considerably more complex in that a number of upper rings are incorporated to help provide specific viewing characteristics.

Finally, U.S. Pat. No. 4,387,992 issued on June 14, 1983 to Swartz shows a cuvette array which is composed of an upper planar member and a number of boat members. These boats are individually attached to the upper planar disc by welding. Because they are permanently attached and because they would have to be cleaned individually, the Swartz array is designed to be disposable. Cleaning of the individual boats would be inefficient. Swartz also makes specific reference to the thickness ratios of the planar member and individual boat walls.

OBJECTS AND SUMMARY OF THE INVENTION

It is a primary object of the present invention to provide a cuvette array which, though low in cost, is reusable.

It is a further object of the present invention to provide a cuvette array which is able to be disassembled easily so as to replace either the bottom cuvette array or upper planar member without having to throw away the entire array structure.

It is another object of the present invention to provide a cuvette array that has an improved cuvette configuration to improve mixing of reactants during testing.

It is still another object of the present invention to provide a cuvette array that may easily be shipped and stored in separate parts.

It is a different object of the present invention to provide a cuvette array which maintains its flexibility and has the ease of use of earlier arrays, without encountering problems with breakage at the corners and edges of the cuvettes individually.

It is yet a different object of the present invention to provide a cuvette array which maintains all of the properties above while using a highly efficient photometric plastic substance.

How these and other objects of the present invention are accomplished will be described in the following specification taken in conjunction with the drawings. Generally, however, the objects are accomplished by providing a rotatable cuvette array for mixing two substances. The array has a circular lower section made of PETG (polyestherethylene-tetraterethalataglycol) plastic with a number of circumferentially spaced cuvettes. Each cuvette has an inner compartment and an outer compartment both of which have upwardly diverging walls, and a ramp separating the two compartments. The edges and corners of the cuvettes are rounded to provide additional strength through increased thickness at those points. The upper section of the cuvette array is a disc made of paperboard laminated with PPF (polyestherpolyethylene film) plastic having alternating opaque and transparent portions providing optic pathways through only the outer compartments of each cuvette. The upper section also includes a number of holes which provide access to the inner and outer compartments of each cuvette for filling. The upper and lower sections are separable to permit cleaning and subsequent reattachment of new upper section so that each lower section of the cuvette array is reusable. Other features of the invention will become apparent to those skilled in the art after reading the following description of the preferred embodiment taken in conjunction with the figures.

DESCRIPTION OF THE DRAWINGS

FIG. 3 is a cross-sectional view of the cuvette array of the present invention taken along the line 3—3 of FIG. 1.

FIG. 4 is an end view of a single cuvette taken along the line 4—4 of FIG. 1.

FIG. 5 is a longitudinal cross-sectional view of an individual cuvette taken along the line 5—5 of FIG. 2.

FIG. 6 is a top plan view of an individual cuvette taken along the line 6—6 of FIG. 5.

DESCRIPTION OF THE PREFERRED EMBODIMENT

Figure 1:
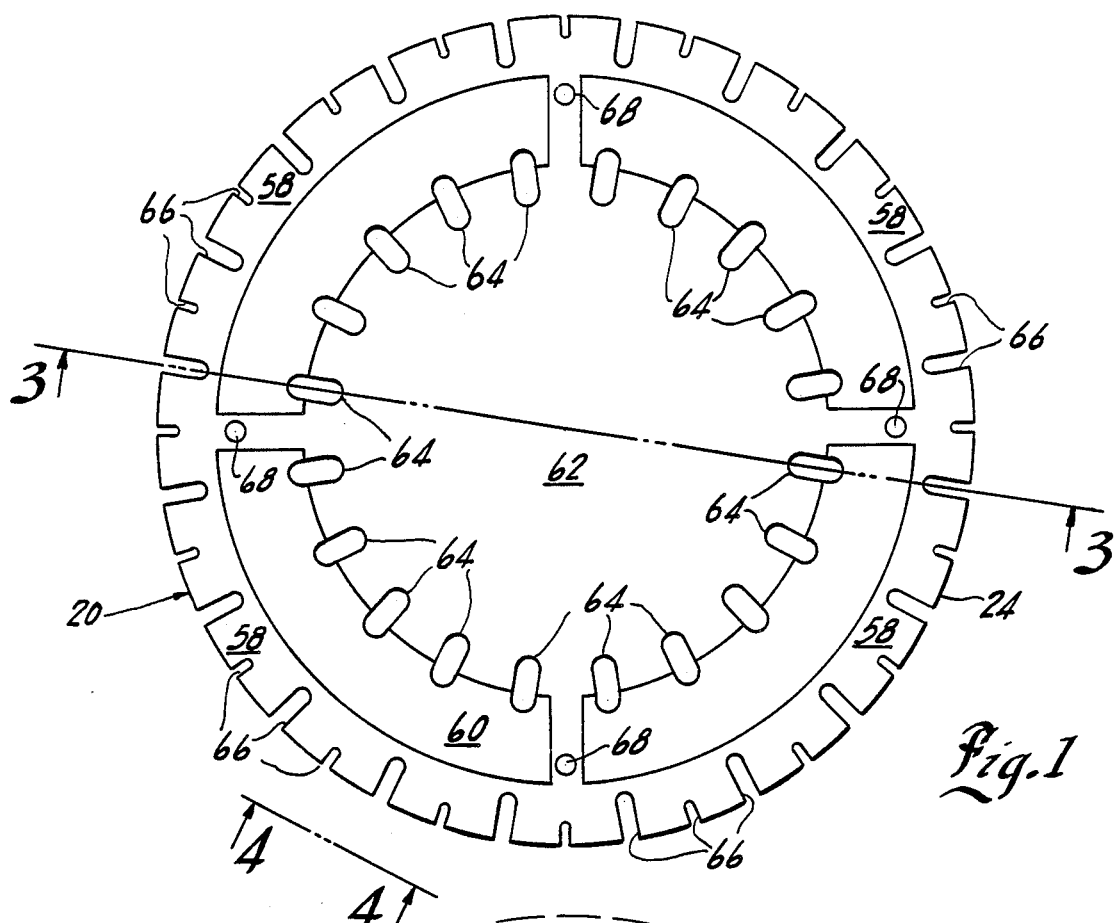
FIG. 1 is a top plan view of a rotatable cuvette array according to the present invention.
Figure 2:
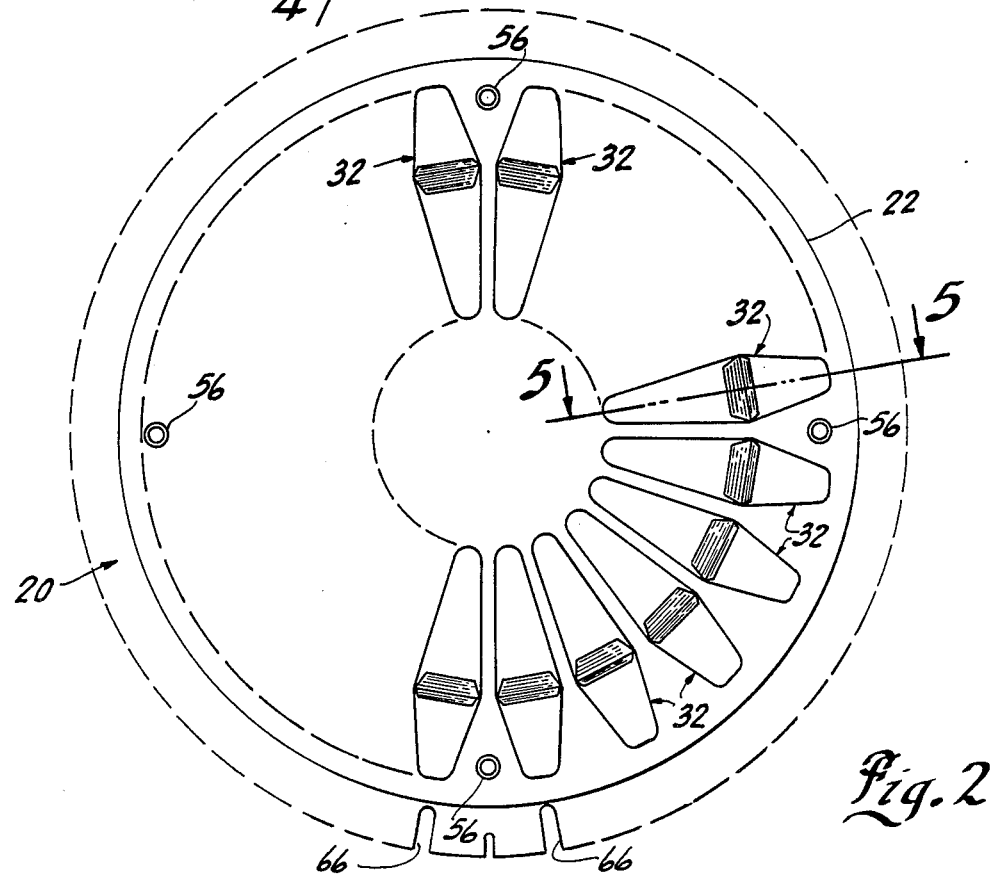
FIG. 2 is a bottom plan view of a rotatable cuvette array according to the present invention.

A cuvette array 20 according to the present invention is shown in FIG. 1. The array 20 is composed of a lower section 22 and an upper planar section 24. The lower surface of upper section 24 and the upper planar surfaces of lower section 22 are joined together by a contact adhesive. This adhesive must be effectively inert with respect to the other materials used to construct the array 20. The contact adhesive permits separation of the two sections 22, 24, thereby permitting easy cleaning and the replacement of either section without having to throw out the entire array disc.

Lower section 22 is formed of PETG plastic. The upper section's transparent portions are PPF plastic. These materials have optical characteristics superior to those of materials used in prior devices. These earlier arrays needed to use materials that were thermoplastic in nature, so that they could be welded together by heat, for example. In addition, the PETG and PPF plastics are considerably less susceptible to scratching and abrasions than the materials used in the past while being able to withstand numerous cleanings. The only limitation on the materials with respect to the present invention is that they cannot react chemically with the contact adhesive.

Lower section 22 is made up of a number of cuvettes 32 which extend radially outward from the center of section 22 and are equidistantly spaced about section 22. Each cuvette 32 has an inner compartment 34 and an outer compartment 36 separated by a ramp 38.

Inner compartment 34 has an inner end wall 40, an outer end wall 42, identical side walls 44 and a bottom wall 46. As can be seen in FIG. 4, side walls 44 are not parallel, but rather diverge upwardly. In the preferred embodiment, these side walls 44 extend upwardly and away from vertical at an angle of approximately 10°. Similarly, the end walls 40, 42 extend upwardly and away from vertical at an angle of 30° in the preferred embodiment as seen in FIG. 5. As seen in FIG. 4 and FIG. 5, the edges and points at which these walls 40, 42, 44 meet are rounded considerably more than in Bullock or other earlier arrays. By providing the angularly oriented walls, the thickness at these edges and corners is approximately four times that of the right angled and unrounded edges and corners of array like Bullock.

The outer compartment 36 also has diverging walls and considerably rounded corners and edges formed with the bottom wall 54. The side walls 48, outer end wall 50, and inner end wall 52 of outer compartment 36 are all oriented at an angle of 10° from vertical in the preferred embodiment. The outer end wall 42 of inner compartment 34 and the inner end wall 42 of outer compartment 36 meet at their top edges, thus forming a ramp 38 between the compartments 34, 36. These end walls 42, 52 do not extend as high vertically as the other walls of the compartments, so that a pathway between the compartments 34, 36 is formed over ramp 38 and below upper section 24.

By increasing the thickness of the edges and corners in the cuvettes 32, the likelihood of the breakage or cracking found in using or attempting to clean the Bullock array is reduced appreciably. In addition, the diverging walls make it easy to nest and denest a large number of lower sections 22 for storage and transportation. The rounded corners also help in providing better mixing of the reactants than would be present with the sharp corners and edges found in earlier arrays like those of Bullock and Tiffany.

Also formed on lower section 22 are a number of lugs 56 situated near the periphery of the array 20. Lugs 56 serve two purposes. First, they can provide a means for securing and orienting the array 20 on the centrifuging equipment. Second, lugs 56 provide a guide for the proper positioning of upper section 24 on lower section 22, as will be explained in more detail below.

Upper section 24 is circular and generally planar. There are three concentric yet distinct regions in section 24: outer opaque ring 58, transparent ring 60, and opaque center disc 62. There are also a number of access holes 64 which will be discussed in more detail below.

The opaque regions 58, 62 are formed by laminating paperboard or another acceptable material with PPF plastic in the process of making section 24. The paperboard helps provide added rigidity to the array 20 as well as eliminating the need for providing a central opaque covering for the array 20 during measuring as required by some earlier arrays. Additionally, there are notches 66 cut at various intervals around the opaque ring 58 of array disc 20. These are standard in most cuvette arrays and are used as an encoding system and to provide a zero referencing for reading during analysis.

The transparent ring 60 is radially wide enough so that accurate reading of the reaction mixture can be made by any appropriate means. The width of the ring therefore extends radially from the series of ramps 38 to a point at or just beyond the outer end wall 50 of each outer compartment 36.

Cut from an area which radially overlaps both the opaque center disc 62 and the transparent ring 60, each access hole 64 is generally elliptical in shape. Its longitudinal axis is centered with the longitudinal axis of the cuvette 32 in the preferred embodiment. Each hole 64 is long enough to provide access to both inner and outer compartments 34, 36 for pipetting substances into those compartments. However, the hole 64 is also the only access to each compartment. Therefore, evaporation and contamination of adjoining cuvettes caused by splashing is greatly reduced. The consequences of any splashing, cross-contamination and evaporation in earlier arrays could be quite severe.

Also cut in upper section 24 are a number of lug holes 68. These holes 68 are provided for matching the lugs 56 of lower section 22 to ensure that the holes 64 are properly aligned with the cuvettes 32. Close tolerances between lugs 56 and holes 68 further ensure that the upper sections 24 can accurately be reattached to the lower sections 22 after separation.

In summary, a cuvette array 20 according to the present invention has two separable sections 22, 24 which may be washed and the bottom section reused. The unique design of the individual cuvettes 32 in lower section 22 prevents excessive breaking and cracking as well as making nesting and denesting of the array discs 20 easy for transportation and storage. The rounded edges and corner provide better mixing than earlier right angle constructions. Upper section 24 has opaque and transparent regions and access holes 64 for filling the cuvettes 32 with the necessary reactants. Because the major portion of each cuvette 32 is covered, however, evaporation and cross-contamination of reactants in adjoining cuvettes is reduced.

It should be obvious to one skilled in the art after reading the present specification that modifications can be made to the present invention without departing from the spirit of the invention. Accordingly, the present invention is not to be limited by the description or illustration of a specific embodiment, but is to be limited solely by the scope of the claims which follow.

I claim:

1. a rotatable cuvette array for mixing two substances and providing the resulting mixture to be analyzed by photometric or flurometric methods, said array comprising:
    a circular lower section comprising a plurality of circumferentially spaced apart cuvettes extending longitudinally from the center of said lower section, each of said cuvettes comprising:
        an inner compartment having a generally horizontal bottom wall, opposing and upwardly diverging side walls, and opposing and upwardly diverging end walls;
        an outer compartment having a generally horizontal bottom wall, opposing and upwardly diverging side walls, and opposing and upwardly diverging end walls; and wherein said outer end wall of said inner compartment and said inner end wall of said outer compartment are attached at their respective top edges thereby forming a ramp, and adjacent edges of said walls defining said compartments forming rounded edges and corners;
    an upper section comprising a generally planar disc having a plurality of holes arranged so that an individual hole corresponds to a single cuvette; and
    an opaque disc, concentric with said lower section, consecutive arcuate segments of the edge of said opaque disc generally coinciding with each of said ramps of each of said cuvettes;
    a generally transparent annulus, the inner edge of said transparent annulus coinciding with the edge of said opaque disc, consecutive arcuate segments of the outer edge of said transparent annulus generally coinciding with each of said outer end walls of said outer compartments; and
    an opaque annulus, the inner edge of said opaque annulus coinciding with the outer edge of said transparent annulus, the outer edge of said opaque annulus generally extending slightly beyond the outer edge of said lower section; and
    said upper and lower sections being separable to permit cleaning of said lower section and subsequent reattachment so as to be reusable.

2. The cuvette array of claim 1 wherein the thickness of the material at said rounded edges and corners is not less than 80% of the thickness of the material at any other point on said array.

3. The cuvette array of claim 1 wherein said opaque disc and annulus of said upper section are integer with said transparent annulus.

4. The cuvettte array of claim 1 wherein each of said holes in said upper section is as small as is necessary to provide access to said inner compartment and said outer compartment of each of said cuvettes for filling.

5. The cuvette array of claim 4 wherein each of said holes is generally elliptical in shape, the longitudinal axis of said hole being parallel to the longitudinal axis of an individual cuvette.

6. The cuvette array of claim 1 wherein said lower section is made of PETG plastic and the transparent portion of said upper section is mad of PPF plastic.

7. The cuvette array of claim 3 wherein, the thickness of the material at said rounded edges and corners is not less than 80% of the thickness of the material at any other point on said array.

8. The cuvette array of claim 7 wherein each of said holes in said upper section is as small as is necessary to provide access to said inner compartment and said outer compartment of each of said cuvettes for filling.

9. The cuvette array of claim 8 wherein each of said holes is generally elliptical in shape, the longitudinal axis of said hole being parallel to the longitudinal axis of an individual cuvette.

10. The cuvette array of claim 9 wherein said lower section is made of PETG plastic and the non-opaque portions of said upper section are composed of PPF plastic.

11. An upper section for a rotatable cuvette array for mixing two substances and providing the resulting mixture to be analyzed by photometric or flurometric methods, said array including a lower section having a plurality of cuvettes extending radially lengthwise, each cuvette having a radially perpendicular ramp separating an inner compartment and an outer compartment, said upper section of said array comprising:
  a generally planar disc having a plurality of holes arranged so that an individual hole corresponds to a single cuvette; and
  said upper section being separable from the remainder of said array so as to permit cleaning of said array and subsequent reattachment of a different upper section so that said lower section is reuseable;
wherein said upper section further comprises:
  an opaque central disc, consecutive arcuate segments of the edge of said opaque disc generally coinciding with each of said ramps of each of said cuvettes;
  a transparent annulus, the inner edge of said transparent annulus coinciding with the edge of said opaque disc, consecutive arcute segments of the outer edge of said transparent annulus generally coinciding with each of the outer ends of said outer cuvettes; and
  an opaque annulus, the inner edge of said opaque annulus coinciding with the outer edge of said transparent annulus.

12. The cuvette array of claim 11 wherein said opaque disc and opaque annulus of said upper section are integral with said transparent annulus.

13. The cuvette array of claim 11 wherein each of said holes in said upper section is as small as is necessary to provide access to said inner compartment and said outer compartment of each of said cuvettes for filling.

14. The cuvettes array of claim 13 wherein each of said holes is generally elliptical in shape, the longitudinal axis of said hole being parallel to the longitudinal axis of an individual cuvette.

15. The cuvette array of claim 11 wherein said lower section is made of PETG plastic and the transparent portion of said uper section is PPF plastic.

16. A rotatable cuvette array for mixing two substances and providing the resulting mixture to be analyzed by photometric or fluorometric methods, said array comprising:
  a circular lower section made of PETG plastic comprising a plurality of circumfernetially spaced apart cuvettes extending longitudinally from the center of said lower section, each of said cuvettes comprising:
    an inner compartment having a generally horizontal bottom wall, opposing and upwardly diverging side walls, and opposing and upwardly diverging end walls;
    an outer compartment having a generally horizontal bottom wall, opposing and upwardly diverging side walls, and opposing and upwardly diverging end walls; and
    wherein said outer end wall of said inner compartment and said inner end wall of said outer compartment are attached at their respective top edges thereby forming a ramp, and adjacent edges of said walls defining said compartments form rounded edges and corners, the thickness of the material at said rounded edges and corners being not less than 80% of the thickness of the material at any other point on said array;
  an upper section made of PPF plastic comprising:
    a generally planar disc having a plurality of holes arranged so that an individual hole corresponds to a single cuvette and is as small as is necessary to provide access to said inner compartment and said outer compartment of each said cuvettes for filling and wherein each of said holes is generally elliptical in shape, the longitudinal axis of said hole being parallel to the longitudinal axis of an individual cuvette;
    an opaque disc, concentric with said lower section, consecutive arcuate segments of the edge of said opaque disc generally coinciding with each of said ramps of each of said cuvettes;
    a generally transparent annulus, the inner edge of said transparent annulus coinciding with the edge of said opaque disc, consecutive arcuate segments of the outer edge of said transparent annulus generally coinciding with each of said outer end walls of said outer compartments; and
    an opaque annulus, the inner edge of said opaque annulus coinciding with the outer edge of said transparent annulus, the outer edge of said opaque annulus generally extending slightly beyond the oute edge of said lower section;
    wherein said opaque disc and annulus of said upper section are integral with said transparent annulus; and
  said upper and lower sections being separable to permit cleaning of said lower section and subsequent reattachment so as to be reusable.

* * * * *